United States Patent
Persson

(10) Patent No.: US 9,943,657 B2
(45) Date of Patent: Apr. 17, 2018

(54) TRACHEOSTOMA VALVE

(71) Applicant: Atos Medical AB, Horby (SE)

(72) Inventor: Jan-Ove Persson, Hoor (SE)

(73) Assignee: Atos Medical AB (SE)

( * ) Notice: Subject to any disclaimer, the term of this patent is extended or adjusted under 35 U.S.C. 154(b) by 685 days.

(21) Appl. No.: 14/386,813

(22) PCT Filed: Mar. 6, 2013

(86) PCT No.: PCT/EP2013/054515
§ 371 (c)(1),
(2) Date: Sep. 21, 2014

(87) PCT Pub. No.: WO2013/139605
PCT Pub. Date: Sep. 26, 2013

(65) Prior Publication Data
US 2015/0083119 A1 Mar. 26, 2015

(30) Foreign Application Priority Data
Mar. 21, 2012 (SE) .................... 1250279-5

(51) Int. Cl.
*A61M 16/04* (2006.01)
*A61M 16/10* (2006.01)
*A61M 16/08* (2006.01)

(52) U.S. Cl.
CPC ...... *A61M 16/0468* (2013.01); *A61M 16/047* (2013.01); *A61M 16/0816* (2013.01); *A61M 16/1045* (2013.01); *F04C 2270/0421* (2013.01)

(58) Field of Classification Search
CPC .......... A61M 16/0468; A61M 16/0816; A61M 16/047; A61M 16/1045; A61M 16/107;
(Continued)

(56) References Cited

U.S. PATENT DOCUMENTS 3,952,335 A 4/1976 Sorce et al.
4,040,428 A 8/1977 Clifford
(Continued)

FOREIGN PATENT DOCUMENTS

CN 1747761 A 3/2006
DE 202008012219 U1 11/2008
(Continued)

OTHER PUBLICATIONS

People's Republic of China Search Report, dated Sep. 25, 2015, 2 pages.

(Continued)

*Primary Examiner* — (Jackie) Tan-Uyen T Ho
*Assistant Examiner* — Margaret Luarca
(74) *Attorney, Agent, or Firm* — Fishman Stewart PLLC

(57) ABSTRACT

A tracheostoma valve for attachment to a tracheostoma valve plaster may include a tubular base portion with a proximal opening through which inhaled and exhaled air enters and exits, respectively. A distal lid portion may be arranged distally of the tubular base portion. The distal lid portion may have a distal opening through which inhaled and exhaled air enters and exits, respectively. The tracheostoma valve may have a valve flap member for closing the distal opening via interaction between a front side of the valve flap member and an edge of the distal opening. A valve retaining arm may be included for interaction with the valve flap member to prevent the valve flap member from interacting with the distal opening.

19 Claims, 5 Drawing Sheets

(58) Field of Classification Search
CPC ....... A61M 16/208; A61M 25/00; A61F 1/20;
F16K 15/14
USPC ............... 128/207.16; 137/115.12, 522, 523;
138/45; 251/95, 103, 107
See application file for complete search history.

(56) References Cited

U.S. PATENT DOCUMENTS

| | | | |
|---|---|---|---|
| 5,059,208 | A | 10/1991 | Coe et al. |
| 5,765,560 | A | 6/1998 | Verkerke et al. |
| 6,138,711 | A * | 10/2000 | Lung-Po ................. B60P 7/065 |
| | | | 137/223 |
| 6,921,417 | B2 | 7/2005 | Persson |
| 2002/0156527 | A1* | 10/2002 | Persson ..................... A61F 2/20 |
| | | | 623/9 |
| 2004/0089291 | A1 | 5/2004 | Persson |

FOREIGN PATENT DOCUMENTS

| | | | | |
|---|---|---|---|---|
| JP | H07-502179 | | 3/1995 | |
| JP | 2003-501141 | A | 1/2003 | |
| JP | 2004-507286 | A | 3/2004 | |
| WO | WO-2011/110549 | A2 | 9/2011 | |
| WO | WO 2011110549 | A2 * | 9/2011 | .......... A61M 16/047 |

OTHER PUBLICATIONS

English abstract for JP-2004-507286.
English abstract JP-H07-502179.

* cited by examiner

TRACHEOSTOMA VALVE

CROSS-REFERENCE TO RELATED APPLICATIONS

This application claims priority to International Patent Application PCT/EP2013/054515 filed Mar 6, 2013 and Swedish Patent Application No. 1250279-5 filed Mar 21, 2012, the contents of which are hereby incorporated by reference in their entirety.

FIELD OF THE INVENTION

The invention relates to a tracheostoma valve adapted to control the flow of air through a tracheostoma comprising a tubular housing having a first end and a second end, said first end being open to be connected to the tracheostoma, a shut-off valve member for closing air flow through the housing from said first end to the ambient atmosphere.

BACKGROUND OF THE INVENTION

Due to diseases of different kinds it is sometimes necessary to remove the larynx by surgery and to open a tracheostoma in order that the individual exposed to the surgery can breathe. By the removal of the larynx the ability to speak will be lost but can be restored to some extent by means of another surgery wherein a fistula is opened up between trachea and esophagus to pass air to the oral cavity via the fistula. A oneway valve is mounted in the fistula. This valve referred to as a voice prosthesis, allows air to pass from trachea to esophagus but blocks completely flow in the opposite direction.

For speech to be generated the tracheostoma must be closed so that air can be pressed from trachea via the voice prosthesis into esophagus the mucous membranes of which are made to vibrate so that speech is produced. The tracheostoma can be closed by covering the tracheostoma with a finger but it is more convenient to use for this purpose a tracheostoma valve of the kind referred to above, which is attached to the neck of the person that has been exposed to tracheostoma surgery, in order to control the connection between trachea and the ambient atmosphere via the tracheostoma.

U.S. Pat. No. 4,582,058 describes a tracheostoma valve wherein the function of the shutoff valve member is controlled by spring bias. This tracheostoma valve requires a relatively high pressure in the housing for keeping the shut-off valve in the closed position during speech, which means that it may be difficult to terminate a sentence when the expiration air from the lungs is ebbing due to the fact that the shut-off valve is unintentionally opened too early. Also, this device is unsuitable for exercising, it comprises a vast amount of components making the manufacturing process difficult and costly, and it has no manual occlusion feature.

U.S. Pat. No. 5,059,208 discloses a patient adjustable valve to control the flow of air through an opening surgically created in the neck of the patient. This device is unsuitable for exercise, since it will close unintentionally when you exhale rapidly. Also, this device has no manual occlusion feature.

WO 01/89618 discloses a tracheostoma valve adapted to control the flow of air through a tracheostoma. The device has a separate adjustable coughing valve with permanent magnets. One of the disadvantages of this device is that it is difficult to close the tracheostoma valve by rapid exhaling, such as when the user is too tired to exhale with sufficient closure rate. Also, this device has no manual occlusion feature. Another problem is that it may be difficult to close the tracheostoma valve when the adhesion between the tracheostoma valve plaster and the skin decreases. Yet a disadvantage is the production cost, resulting from the use of several and expensive parts, such as the permanent magnets. Additionally, this device is noisy, due to the change of air direction in the device.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a tracheostoma valve for attachment to a tracheostoma valve plaster, comprising: a tubular base portion with a proximal opening through which inhaled and exhaled air may exit and enter, respectively, the tracheostoma valve; a distal lid portion arranged distally of the tubular base portion, said distal lid portion having a distal opening through which inhaled and exhaled air may enter and exit, respectively, the tracheostoma valve; a valve flap member for closing the distal opening via interaction between a front side of said valve flap member and the edge of the distal opening; and a valve retaining arm for interaction with said valve flap member to prevent said valve flap member from interacting with said distal opening, according to the appended patent claims.

Further advantageous features of the tracheostoma valve of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on an embodiment of the present invention applicable to a tracheostoma valve. The tracheostoma valves according to the prior art are accompanied with several disadvantages, such as unsatisfactory performances and high prices. For example, the tracheostoma valves do not have set position in which free breathing through the tracheostoma valve, without the risk of closing the tracheostoma valve at high expiration flow rate. The present invention aims at solving these problems.

Figure 1:
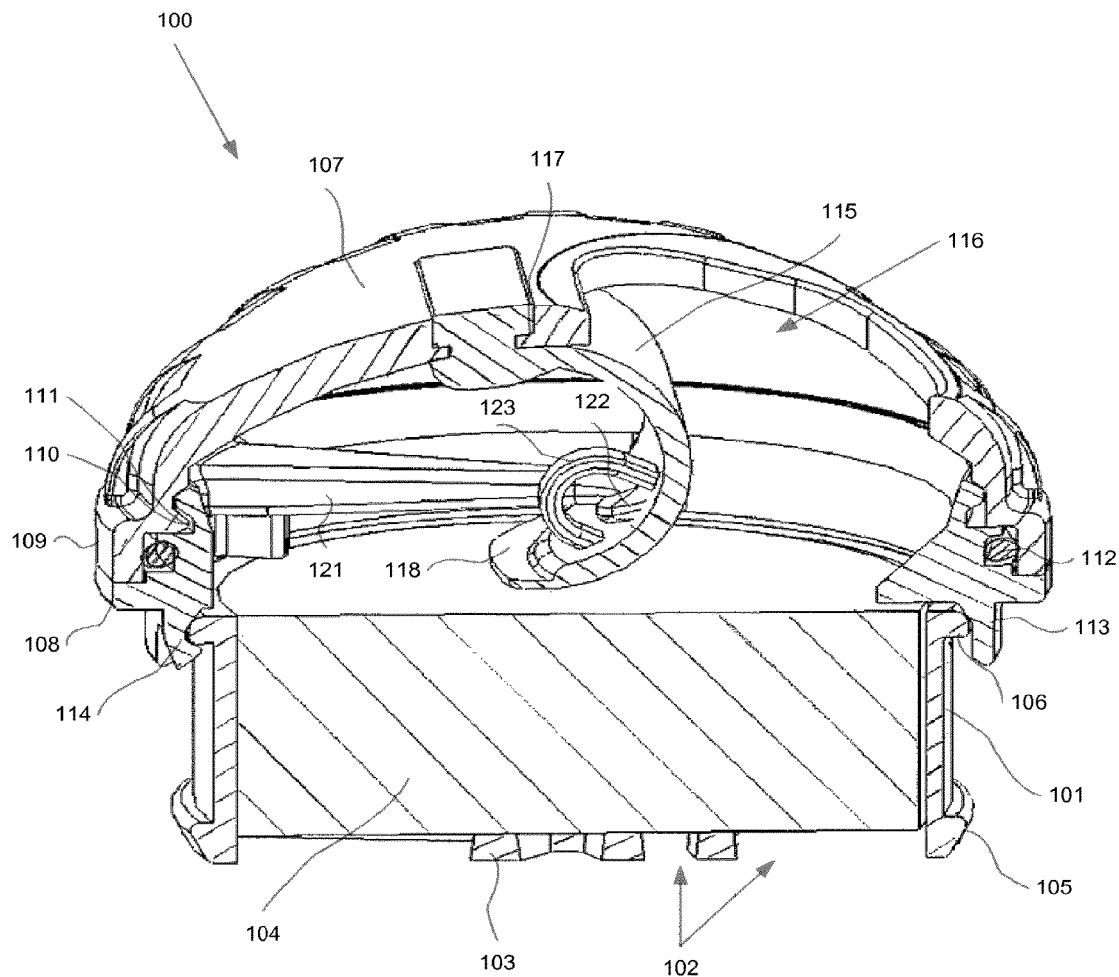
FIG. 1 is a cross-sectional view along a substantially longitudinal plane of a an embodiment of the invention.

In FIG. 1, a tracheostoma valve 100 according to one embodiment is disclosed. The tracheostoma valve 100 comprises a tubular base portion 101. The tubular base portion 101 may preferably be made of a hard plastic material, such as polypropylene. The tubular base portion 101 has a proximal opening 102, through which inhaled and exhaled air may enter and exit, respectively, the tracheostoma and thus the lungs of the patient. At the proximal end a grid or bar structure 103 may cover the proximal opening 102, such that air may pass through the intervening space. The lumen of the tubular base portion 101 is sized and dimensioned to house a heat and moisture exchanger (HME) 104. The HME 104 may for example be an impregnated polyurethane foam. Radially outwards from the proximal end of the tubular base portion 101 a fixation flange 105 may be positioned. The fixation flange 105 is adapted in size and dimensions for cooperating with a corresponding recess in a tubular receiving means of a tracheostoma plaster (not shown). At the distal end of the tubular base portion 101 a distal rim 106 is protruding radially outwards of the base portion 101. The distal rim 106 serves as an interconnection rim with a distal lid portion 107, to be applied distally of the base portion 101.

The distal lid portion 107 may comprise a proximal coupling part 108 and a distal lid part 109. The coupling part 108 may be of a low friction plastic material, such as polyacetal, such as Delrin®. The distal lid part 109 may preferably be made of a hard plastic material, such as polypropylene. The coupling part 108 may be connected to the lid part 109 through a snap-on fit, comprising a rim 110 on the lid part 109 and a corresponding track 111 on the coupling part, and a sealing element in form of a sealing o-ring 112 between the coupling part 108 and the lid part 109, for hindrance of air leakage between the two. The coupling part 108 is ring-shaped, with a central lumen, such that exhaled or inhaled air may pass through the coupling part 108 to the environment or lungs, respectively. The coupling part 108 may have a proximal rail portion 113, with a recess 114 situated on the internal side for snap-on fitting with the distal rim 106 of the base portion 101. The coupling part 108 is snap-on fitted to the base portion 106 in a manner such that the coupling part and the base portion 106 not may be rotated in relation to each other. This may be accomplished with one or more protrusions on either the coupling part 108 or the base portion 101, interacting with one or more corresponding recesses on the other part of the two.

The coupling part 108 and the distal lid part 109 are rotatable in relation to each other around the central axis of the tracheostoma valve 100 between at least two positions. These positions comprise a first position in which a valve flap member 115 is active, i.e. a speaking mode in which the valve flap member may close the tracheostoma valve 100, and a second position in which the valve flap member may be non-active, i.e. exercising mode in which the valve flap member may not close the tracheostoma valve 100.

The distal lid part 109 is provided with an exhaling outlet in form of an opening 116. The shape of the lid part 109 may be dome or cone shaped, and the opening 116 may be positioned on the slanting surface of the distal lid part 109, such that the plane of the opening is angled in relation to the transversal plane of the tracheostoma valve 100. In this way the risk of clothes clogging the opening 116 is significantly reduced. Thus it is preferable that the opening is positioned displaced in relation to the central axis of the tracheostoma valve 100. This also facilitates finger closing of the opening 116. For further facilitation of finger closing of the opening 116, the opening 116 may have an oval shape in the proximodistal/longitudinal direction. The valve flap member 115 is attached to the lid part 109 via a slot 117 at the top of the lid part 109. In this way, the valve flap member may be replaced in a convenient manner once worn out. The valve flap member 115 may have a peripheral flange 118. The peripheral flange 118 may have a thickness smaller than central portions of the valve flap member 115. The peripheral flange 118 enhances sealing in speaking mode, when the peripheral flange 118 interacts with the edge of the opening 116, since the thicker part of the valve flap member 115 will also protrude into the opening 116, such that the interaction area between the edge of the opening 116 and the valve flap member 115 is increased. The thin peripheral flange 118 of the valve flap member 115 also allows for coughing release, since the valve flap member 115, during increased exhalation air speed, such as during coughing, may be forced through the opening 116 in a facilitated manner. The user may then easily push the valve flap member 115 into the tracheostoma valve 100 with the his/her finger. A suitable material for the valve flap member 115 is silicone or other flexible materials.

Figure 2:
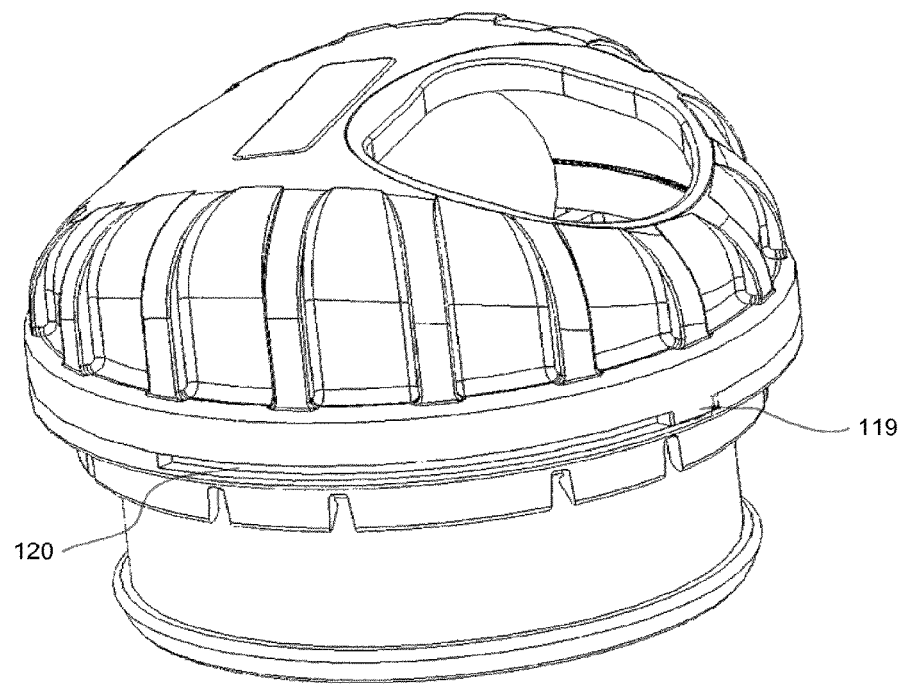
FIG. 2 is a perspective view of an embodiment of the invention.

As disclosed in FIG. 2, the distal lid part 109 is provided with a peripheral tap 119 extending in the proximal direction. The tap 119 runs in a corresponding peripheral and distal groove 120 on the coupling part 108, such that the lid part 109 may be rotated with respect to the coupling part 108 between at least said two positions. The first position is reached when the tap 119 hits one end of said groove 120 and the second position is reached when the tap 119 hits the other end of said groove 120. In this way, due to the coupling part 108 is mounted in a non-rotatable manner on said base portion, the lid part 109 may be rotated between said first and second positions with regard to the coupling part 108. Instead of one tap 119 the distal lid part 109 may of course be provided with two (or more) taps, whereby a first tap hits one end of said groove 120 to when the first position is reached, while the second tap hits the other end of said groove 120 when the second position is reached.

Turning again to FIG. 1, a valve retaining arm 121 is extending from the coupling part 108 in the transversal plane with regard the central axis of the tracheostoma valve 100 from the periphery and inwardly. The retaining arm 121 extends in the transversal plane distally of the HME 104. At the end of the retaining arm 121 a retaining hook 122 is positioned. The retaining arm 121 with the retaining hook 122 is intended to interact with a loop 123 on the valve flap member 115, such that when the retaining hook 122 interacts with the loop 123, the valve flap member will be hindered from interrupting the air flow through the tracheostoma valve 100. In this position the user of the tracheostoma valve may for example exercise freely, with no risk of sudden interruption of the air flow through the tracheostoma valve 100.

Since the tracheostoma valve 100 has a finger closable opening 116 and a valve flap member 115, interacting with the inner edger of the opening 116 upon increased exhalation air speed, when the valve flap member not is hindered from interrupting the air flow through the tracheostoma valve 100, the tracheostoma valve 100 uniquely combines two positive user modes, thus creating a more versatile tracheostoma valve.

Figure 3:
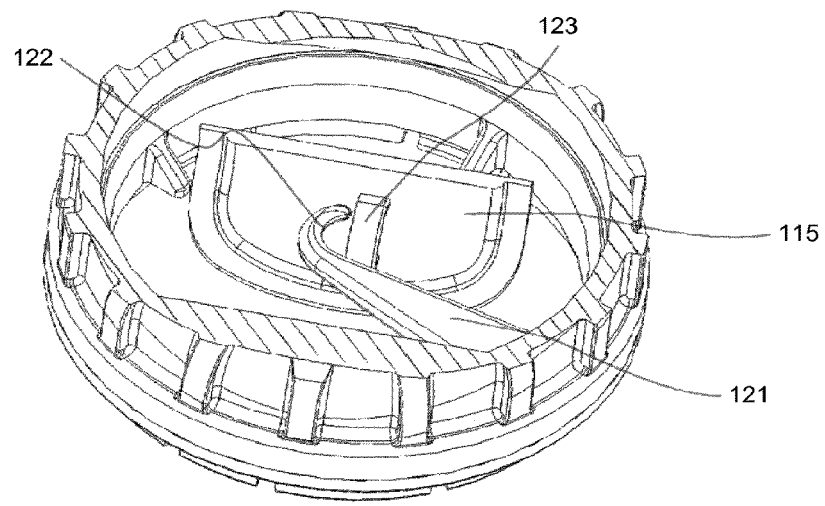
FIG. 3 is a cross-sectional view along a substantially transversal plane of an embodiment of the invention.

In FIG. 3, it is disclosed when the tracheostoma valve 100 is in said first position, i.e. speaking mode. In this position the lid part 109 has been rotated with regard to the coupling part 108, as disclosed above, such that the retaining hook 122 is separated from the loop 123. In this position the valve flap member 115 may be freely affected by the exhaled air to close the opening 116, such that exhaled air instead is forced through a voice prosthesis in the oesophagal wall, between trachea and oesophagus.

Figure 4:
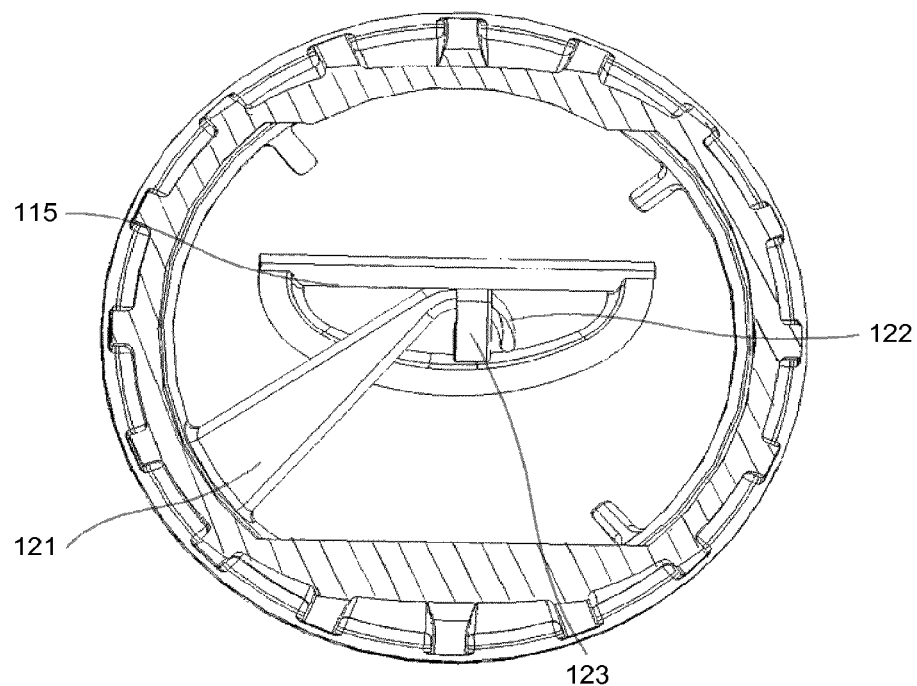
FIG. 4 is a cross-sectional view along a substantially transversal plane of an embodiment of the invention.

When rotating the lid part 109 from said first position into said second position, i.e. exercising mode, the retaining hook 122 interacts with the loop 123, such that the retaining hook 122 will enter the loop 123. When the user then releases the valve flap member 115 with his/her finger, the valve flap member 115 will be maintained in said second position, i.e. exercise mode. This is disclosed in FIG. 4. If the user still wants to speak when the tracheostoma valve is in said second position, the user may place his/her finger over the opening 116 to close the outlet, whereby exhaled air instead will exit through the voice prosthesis in accordance with above. This also allows for actuating a force onto the device and the plaster beneath, such that the outlet is closed with the finger of the user while simultaneously the plaster is pressed against the skin surrounding the tracheostoma, whereby also a sealing effect may be obtained between an ill-adhered plaster and the skin.

Figure 5:
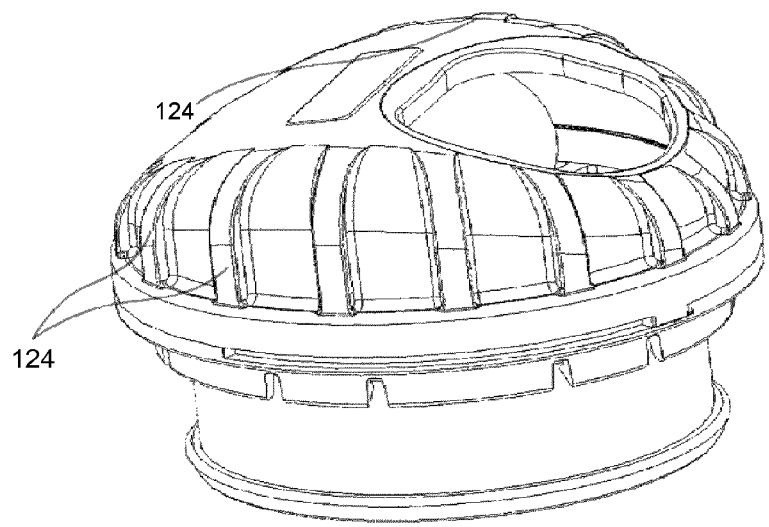
FIG. 5 is a perspective view of an embodiment of the invention.

The distal lid portion 107, such as the distal lid part 109, may be provided with outer gripping ribs 124, in accordance with FIG. 5, extending from the periphery towards the top of the lid portion 107, such that they will traverse the rotational direction when the lid portion 107 or lid part 109 is twisted between the first and second positions. These ribs 124 will then extend substantially longitudinally of the tracheostoma valve 100. In this way the grip may be increased.

In another embodiment the retaining arm 121 may be positioned on the base portion 101 and the coupling part 108 may be omitted. In this embodiment the base portion 101 and the distal lid portion 107 are rotatably engaged, in a similar way as the coupling part 108 and the lid part according to the embodiment above, such that the base portion 101 and the lid portion 107 may be rotated between at least two positions in relation to each other.

Figure 6:
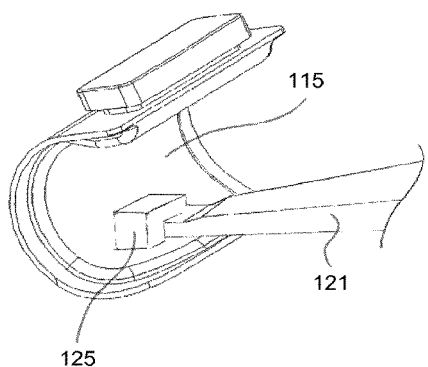
FIG. 6 is a perspective view of a valve flap member and a valve retaining arm of an embodiment of the invention.

Instead of a loop 123 the backside of the valve flap member 115 may be provided with another form of retaining arm connector, such as a retaining pocket 125, which the retaining arm 121 may enter in a retaining way upon rotation of the retaining arm 121 in relation to the retaining arm connector, in accordance with FIG. 6.

Figure 7:
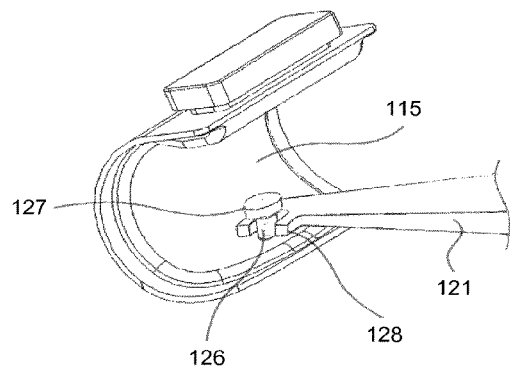
FIG. 7 is a perspective view of a valve flap member and a valve retaining arm of an embodiment of the invention.

The valve flap member 115 may also be provided with retaining arm connector in form of a protruding pin 126, which the retaining arm 121 may retainingly engage with, upon rotation of the retaining arm 121 in relation to the retaining arm connector, in accordance with FIG. 7. The protruding pin 126 may be provided with an end flange 127, securing better cooperation between the retaining arm 121 and the pin 126. The retaining arm 121 may then be provided with a hook element 128, corresponding in hook cut-out with the diameter of the pin 126.

Figure 8:
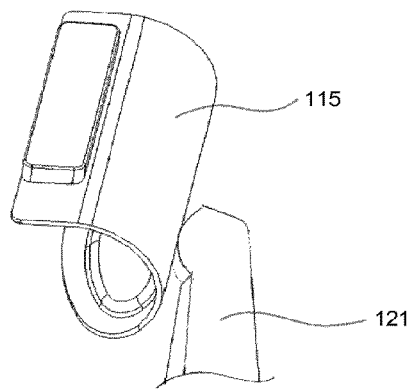
FIG. 8 is a perspective view of a valve flap member and a valve retaining arm of an embodiment of the invention.

Alternatively the retaining arm connector 121 is simply arranged such that it, upon rotation of the retaining arm 121 in relation to the valve flap member 115, hinders the valve flap member 115 from further movement towards the distal opening 116, such that it is hindered from closing said distal opening 116, in accordance with FIG. 8, even though this embodiment does not assure as safe closing prohibition as embodiments with retaining arm connectors, according to FIGS. 1 to 7.

Figure 9:
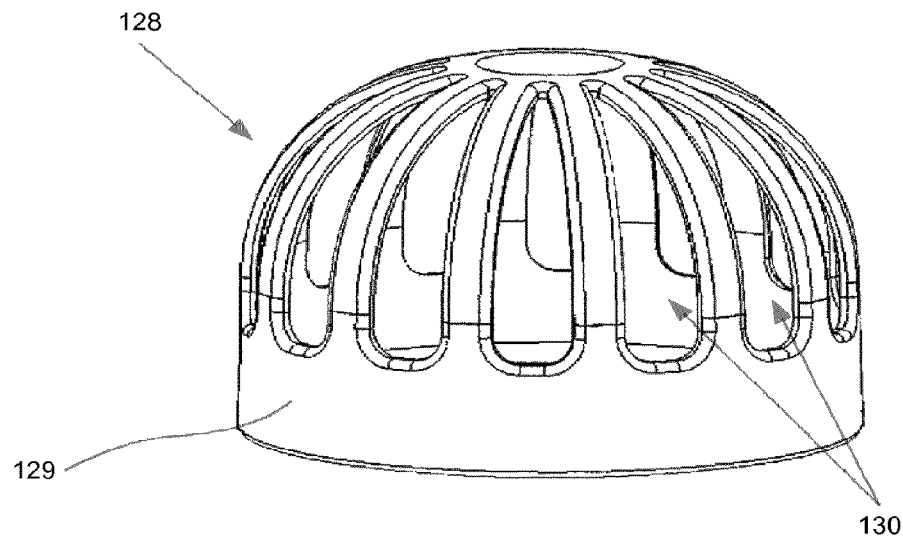
FIG. 9 is a perspective view of a filter casing of an embodiment of the invention.
Figure 10:
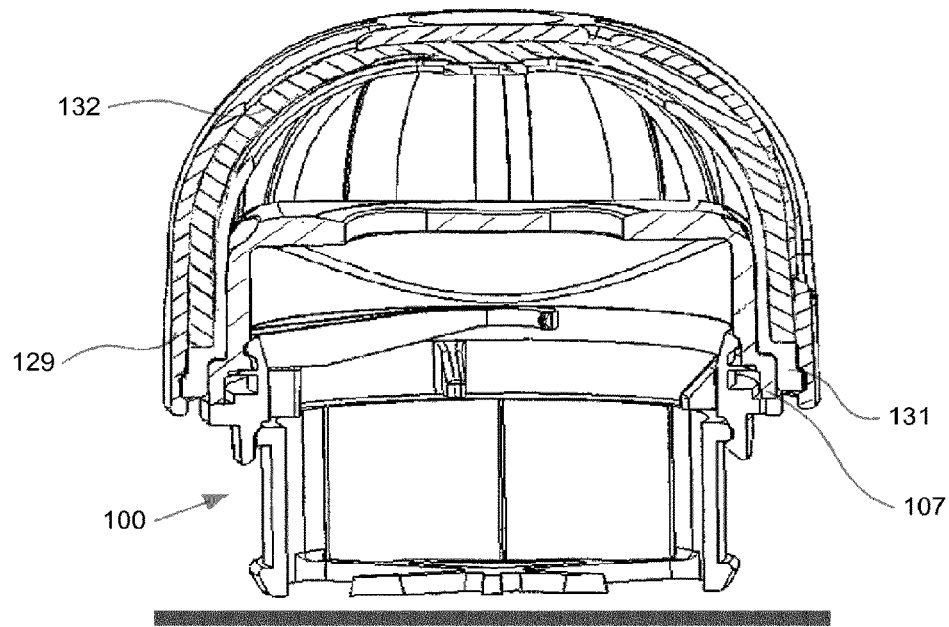
FIG. 10 is a cross-sectional view along a substantially longitudinal plane of a an embodiment of the invention.

In FIG. 9 a filter casing 128 is disclosed in a perspective view. The filter casing 128 is adapted to be arranged on the tracheostoma valve 100, according to the embodiments disclosed in FIGS. 1 to 7. In FIG. 10 a cross-sectional view along a substantially longitudinal plane of the filter casing 128 is disclosed. The filter casing 128 comprises an outer support structure 129, with apertures 130 for allowing air to enter and exit the filter casing 128 and thus also the tracheostoma valve 100 upon which it is arranged. The outer support structure may be dome-shaped. Inside the outer support structure 129, an inner support structure 131 is arranged. Also the inner support structure 129 is provided with apertures, for allowing air to enter and exit the filter casing 128, and thus the tracheostoma valve 100 upon which the filter casing 128 is arranged. The inner support structure 131 substantially follows the inner contour of the outer support structure 129, at a distance there from to allow for a filter 132 to be arranged between the outer support structure 129 and the inner support structure 131. In this way the filter 132 may follow the inner contour of the outer support structure 129, such that its surface area may substantially correspond to the inner extension of the outer support structure 129. In this way, when the outer support structure is dome-shaped, the surface area of the filter 132 may be optimized. The filter 132 may be an electrostatic filter. The outer support structure 129 may be snap-fitted onto the inner support structure 131 along the proximal circumference of the inner support structure 131. In turn the filter casing 128 may be snap-fitted onto the tracheostoma valve 100 via snap-fitting the inner circumference of the inner support structure 131 onto the circumference of the tracheostoma valve 100, such as onto the circumference of the distal lid portion 107.

The elements and components of an embodiment of the invention may be physically, functionally and logically implemented in any suitable way. Indeed, the functionality may be implemented in a single unit, in a plurality of units or as part of other functional units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor.

Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A tracheostoma valve for attachment to a tracheostoma valve plaster, comprising:
    a tubular base portion with a proximal opening through which inhaled and exhaled air exits and enters, respectively;
    a distal lid portion arranged distally of the tubular base portion, said distal lid portion having a distal opening through which inhaled and exhaled air enters and exits, respectively;

a valve flap member for closing the distal opening via interaction between a front side of said valve flap member and an edge of the distal opening; and a valve retaining arm for interaction with said valve flap member to prevent said valve flap member from interacting with said distal opening, wherein the valve retaining arm is rotatable in a transversal plane of the tracheostoma valve between at least a first and a second position, for allowing interaction and release of the valve flap member in said first and second position, respectively.

2. The tracheostoma valve according to claim 1, wherein the distal lid portion and the base portion are rotatable in relation to each other, and the valve flap member is arranged on the lid portion and the valve retaining arm is arranged on the base portion.

3. The tracheostoma valve according to claim 1, wherein the distal lid portion includes a proximal coupling part for connection to the base portion and a distal lid part, wherein the coupling part and the lid part are rotatable in relation to each other, and the valve flap member is arranged on the lid part and the valve retaining arm is arranged on the coupling part.

4. The tracheostoma valve according to claim 3, wherein a sealing element is positioned between the coupling part and the lid part.

5. The tracheostoma valve according to claim 3, wherein the lid part is provided with a peripheral tap extending in a proximal direction, the tap running in a corresponding peripheral and distal groove on the coupling part, such that the lid part is rotatable with respect to the coupling part between at least said two positions.

6. The tracheostoma valve according to claim 1, further comprising a heat and moisture exchanger housed in the base portion.

7. The tracheostoma valve according to claim 1, wherein the base portion a proximal end includes at least one of a grid and a bar structure.

8. The tracheostoma valve according to claim 1, further comprising a fixation flange extending radially outwards from a proximal end of the tubular base portion, for cooperation with a corresponding recess in a tracheostoma plaster.

9. The tracheostoma valve according to claim 1, wherein the base portion includes a distal rim, protruding radially outwards of the base portion, for cooperation with the lid portion.

10. The tracheostoma valve according to claim 9, wherein the lid portion includes a proximal rail portion, with a recess situated on an internal side of the rail portion for cooperation with the distal rim of the base portion.

11. The tracheostoma valve according to claim 1, wherein the lid portion has a slanting distal top surface, and the distal opening is positioned on said slanting surface of the distal lid par, such that the plane of the opening is angled in relation to a transversal plane of the tracheostoma valve.

12. The tracheostoma valve according to claim 1, wherein the valve flap member is attached to the lid portion via a slot.

13. The tracheostoma valve according to claim 1, wherein the valve flap member has a peripheral flange and a loop configured to receive a retaining hook of the retaining arm.

14. The tracheostoma valve according to claim 1, wherein said valve flap member includes a connector on a back side of said valve flap member; and the valve retaining arm is configured for interaction with said connector to prevent said valve flap member from interacting with said distal opening.

15. The tracheostoma valve according to claim 14, wherein the retaining arm is provided with a retaining hook at a free end for cooperation with said connector in form of a protrusion.

16. The tracheostoma valve according to claim 15, wherein the protrusion is a loop.

17. The tracheostoma valve according to claim 1, wherein the distal lid portion is provided with outer gripping ribs, extending from the periphery towards the top of the lid portion, such that the gripper ribs traverse a rotational direction when the lid portion is twisted between the first and second positions.

18. The tracheostoma valve according to claim 1, further comprising a filter casing arranged distally on top of the distal lid portion.

19. The tracheostoma valve according to claim 18, wherein the filter casing includes an outer support structure, an inner support structure, and a filter arranged in between said outer support structure and said inner support structure.

* * * * *